(12) United States Patent
Pautot

(10) Patent No.: US 9,311,702 B2
(45) Date of Patent: Apr. 12, 2016

(54) SYSTEM AND METHOD FOR ESTIMATING A QUANTITY OF INTEREST OF A DYNAMIC ARTERY/TISSUE/VEIN SYSTEM

(75) Inventor: Fabrice Pautot, La Ciotat (FR)

(73) Assignee: OLEA MEDICAL, La Ciotat (FR)

(*) Notice: Subject to any disclaimer, the term of this patent is extended or adjusted under 35 U.S.C. 154(b) by 0 days.

(21) Appl. No.: 14/240,239

(22) PCT Filed: Aug. 24, 2012

(86) PCT No.: PCT/FR2012/051935
§ 371 (c)(1),
(2), (4) Date: Apr. 7, 2014

(87) PCT Pub. No.: WO2013/030500
PCT Pub. Date: Mar. 7, 2013

(65) Prior Publication Data
US 2014/0219532 A1    Aug. 7, 2014

(30) Foreign Application Priority Data

Aug. 26, 2011 (FR) ................................ 11 57578

(51) Int. Cl.
| | |
|---|---|
| *G06K 9/00* | (2006.01) |
| *G06T 7/00* | (2006.01) |
| *A61B 5/00* | (2006.01) |
| *A61B 5/055* | (2006.01) |

(Continued)

(52) U.S. Cl.
CPC ............ *G06T 7/0012* (2013.01); *A61B 5/0042* (2013.01); *A61B 5/055* (2013.01); *A61B 6/507* (2013.01); *G01R 33/56366* (2013.01); *G06F 17/12* (2013.01); *G06F 17/16* (2013.01); *G06T 7/0016* (2013.01); *A61B 5/0263* (2013.01); *A61B 2576/026* (2013.01); *G06T 2207/10081* (2013.01); *G06T 2207/10088* (2013.01); *G06T 2207/30016* (2013.01); *G06T 2207/30048* (2013.01); *G06T 2207/30101* (2013.01); *G06T 2207/30104* (2013.01)

(58) Field of Classification Search
None
See application file for complete search history.

(56) References Cited

U.S. PATENT DOCUMENTS

| | | |
|---|---|---|
| 2007/0112264 A1 | 5/2007 | Wu et al. |
| 2008/0300484 A1 | 12/2008 | Wang et al. |

(Continued)

FOREIGN PATENT DOCUMENTS

| | | | |
|---|---|---|---|
| WO | WO 2005/009204 A2 | 2/2005 | |
| WO | WO 2005009204 A2 * | 2/2005 | ........... A61B 5/0263 |

OTHER PUBLICATIONS

International Search Report (PCT/ISA/210) mailed on Nov. 2, 2012, by the European Patent Office as the International Searching Authority for International Application No. PCT/FR2012/051935.

(Continued)

*Primary Examiner* — Avinash Yentrapati
(74) *Attorney, Agent, or Firm* — Buchanan Ingersoll & Rooney PC

(57) ABSTRACT

The invention relates to a system and a method for estimating a quantity of interest of a dynamic artery/tissue/vein system of an elementary volume—referred to as a voxel—of an organ based on medical images according to the methods referred to as oSVD or cSVD. The invention discloses two embodiments which are distinguished by the execution time necessary in order to produce the estimate of said quantity of interest and enable a therapeutic diagnosis including in an emergency situation.

14 Claims, 4 Drawing Sheets

(51) Int. Cl.
  *G01R 33/563* (2006.01)
  *G06F 17/12* (2006.01)
  *G06F 17/16* (2006.01)
  *A61B 6/00* (2006.01)
  *A61B 5/026* (2006.01)

(56) References Cited

U.S. PATENT DOCUMENTS

2012/0141005 A1* 6/2012 Djeridane .......... A61B 5/02028 382/131
2013/0266201 A1* 10/2013 Pautot ................ A61B 5/02028 382/131
2014/0219532 A1* 8/2014 Pautot ................ A61B 5/0042 382/131

OTHER PUBLICATIONS

Written Opinion (PCT/ISA/237) mailed on Nov. 2, 2012, by the European Patent Office as the International Searching Authority for International Application No. PCT/FR2012/051935.

Wu et al., "Tracer arrival timing-insensitive technique for estimating flow in MR perfusion-weighted imaging using singular value decomposition with a block-circulant deconvolution matrix", Magnetic Resonance in Medicine, Jul. 1, 2003, pp. 164-174, vol. 50, No. 1.

Gall et al., "On the design of filters for fourier and oSVD-based deconvolution in bolus tracking perfusion MRI", Magnetic Resonance Materials in Physics, Biology and Medicine, May 20, 2010, pp. 187-195, vol. 23, No. 3.

* cited by examiner ial diagnosis in an emergency situation.
SYSTEM AND METHOD FOR ESTIMATING A QUANTITY OF INTEREST OF A DYNAMIC ARTERY/TISSUE/VEIN SYSTEM The invention relates to a system and a method for estimating haemodynamic parameters based on medical images. The invention is distinguished in particular from known processes by its precision and depending upon the embodiment by a speed of execution, which is essential in order to enable a therapeutic diagnosis in an emergency situation.

The invention is based in particular on perfusion-weighted magnetic resonance imaging (PW-MRI) or computed tomography (CT). These techniques make it possible to obtain precious information about the haemodynamics of organs such as the brain or the heart. This information is particularly crucial for a practitioner seeking to make a diagnosis and a therapeutic decision in the emergency treatment of pathologies such as strokes.

In order to implement such techniques, a medical imaging system is used such as is illustrated by way of example by FIGS. 1 and 2 using an apparatus 1 for imaging by nuclear magnetic resonance or by computed tomography. This latter delivers a plurality of sequences of digital images 12 of a first part of the body, in particular the brain. For this purpose said apparatus applies a combination of high-frequency electromagnetic waves on the part of the body in question and measures the signal re-emitted by certain atoms. Thus the apparatus makes it possible to determine the chemical composition and therefore the nature of the biological tissues at each point (or voxel) of the imaged volume.

Sequences of images are analysed by means of a dedicated processing unit 4. This processing unit ultimately delivers to a practitioner 6 an estimation of the haemodynamic parameters on the basis of perfusion weighted images, by means of an adapted men-machine interface 5. Thus the practitioner can reach a diagnosis and decide on the therapeutic action which he deems suitable.

Perfusion-weighted images by nuclear magnetic resonance or by computed tomography are obtained by injecting a contrast agent (for example a gadolinium salt for Magnetic Resonance Imaging) intravenously and by recording its bolus over time in each voxel of the image. For the sake of concision, we will omit the indices x,y,z in order to identify voxels. For example, instead of denoting as $S_{x,y,z}(t)$ the signal for a voxel of co-ordinates x,y,z, we will simply denote it as S(t). It is understood that the operations and the calculations described below are generally performed for each voxel of interest, so as to eventually obtain images or maps which represent the haemodynamic parameters to be estimated.

A standard model makes it possible to link the intensity of the signals S(t) measured over time t to the concentration C(t) of said contrast agent.

For example, in perfusion computed tomography, the signal for each voxel is assumed to be directly proportional to the concentration: $S(t)=k \cdot C(t)+S_0$. In perfusion weighted imaging by nuclear magnetic resonance, it is assumed for example that there is an exponential relationship $S(t)=S_0 \cdot e^{-k \cdot TE \cdot C(t)}$. In the two cases, $S_0$ represents the average intensity of the signal before the arrival of the contrast agent. In the case of nuclear resonance magnetic imaging, k is a constant depending upon the relationship between the paramagnetic susceptibility and the concentration of the contrast agent in the tissue and TE is the echo time. As the value of the constant k for each voxel is unknown, it is set to an arbitrary value for all voxels of interest. Thus relative estimates are obtained, but not absolute estimates. Nevertheless this relative information remains relevant since the interest lies principally in the relative variation of these values in space, in particular between healthy and pathological tissues.

In all that follows we will assume the experimental intensity signals S(t) as previously converted into concentration curves C(t). For example, in the case of perfusion weighted magnetic resonance imaging we have $$C(t) = -\ln \frac{S(t)}{S_0},$$

$S_0$ being estimated by taking, for example, the average value of S(t) before the arrival of the contrast agent. The conservation of the mass of the contrast agent in the volume of tissue contained in each voxel at each instant is written as $$\frac{dC(t)}{dt} = BF \cdot [C_a(t) - C_v(t)].$$

$C_a(t)$ is the concentration of the contrast agent in the artery which supplies the volume of tissue (Arterial Input Function, AIF). BF is the blood flow in the volume of tissue and $C_v(t)$ is the concentration of the contrast agent in the vein draining the volume of tissue (Venous Output Function, VOF).

Assuming the dynamic artery/tissue/vein system to be linear and time invariant, it is possible to write Cv(t)=Ca(t) ⊗ h(t) where h(t) is the system impulse response—or else the probability density function of the transit time of the contrast agent in the tissue—and ⊗ designates the convolution product. A formal solution of the preceding differential equation with initial condition C(t=0)=0 is then written as C(t)=BF·Ca(t)⊗ R(t) where R(t) is the complementary cumulative density/distribution function of the transit time in the volume of tissue (residue function) defined by $$R(t) = H(t) - \int_0^t h(\tau) d\tau$$

where H is the Heaviside unit step generalised function. On the basis of the impulse response and the complementary cumulative density/distribution function, a new haemodynamic parameter is defined, the mean transit time in the tissue (MTT):

$$MTT = \int_0^{+\infty} t \cdot h(t) dt = \int_0^{+\infty} R(t) dt$$

$$\left( \text{if } \lim_{t \to \infty} t \cdot h(t) = 0 \right.$$

Likewise the blood volume (BV) in the tissue volume tissue can be defined by the relationship BV=BF·MTT.

If the AIF used is delayed by a time period τ in relation to the real AIF, we have C(t)=BF·Ca(t−τ)⊗ R(t)=BF Ca(t) ⊗ R(t−τ).

Thus the time period τ can be considered in practice as the time point where the estimated complementary cumulative density/distribution function reaches its maximum (time to maximum—TMAX).

In order to estimate the haemodynamic parameters such as BF, MTT, BV or TMAX as well as the cumulative density/distribution function complementary R(t), it is therefore necessary to deconvolute the concentration curves C(t) by arterial input functions $C_a(t)$ which are assumed as given below.

In order to perform this operation of deconvolution of C(t) by $C_a(t)$, the standard convolution model C(t)=BF·Ca(t) ⊗ R(t) is first of all discretised temporally at the times $t_1, \ldots, t_N$ of sampling of the signal S(t), by numerically approaching the convolution integral Ca(t)⊗ R(t). Without loss of generality, we will assume below that periodic sampling is performed, with period $\Delta t = t_i - t_{i-1}$.

For example, the approximation of the convolution integral by the rectangles method gives $$\forall i = 1, N,$$
$$C(t_i) = BF \cdot \int_0^{t_i} C_a(\tau) \cdot R(t-\tau) d\tau \approx BF \cdot \Delta t \cdot \sum_{k=0}^{i} C_a(t_i) \cdot R(t_i - t_k)$$

Thus we arrive at a linear system Ad=c of dimension N by posing $$A = \Delta t \cdot \begin{pmatrix} C_a(t_1) & 0 & \ldots & 0 \\ C_a(t_2) & C_a(t_1) & \ddots & \vdots \\ \vdots & \vdots & \ddots & 0 \\ C_a(t_N) & C_a(t_{N-1}) & \ldots & C_a(t_1) \end{pmatrix},$$

$$b = \begin{vmatrix} R(t_1) \\ R(t_2) \\ \ldots \\ R(t_N) \end{vmatrix},$$

$$c = \begin{vmatrix} C(t_1) \\ C(t_2) \\ \ldots \\ C(t_N) \end{vmatrix}$$

and d=BF·b.

The lower triangular Toeplitz matrix A is very poorly conditioned and almost singular, so that one cannot numerically invert the linear system without obtaining meaningless solutions and aberrant estimates of haemodynamic parameters. It is therefore necessary to use various methods in order to obtain for example a pseudo-inverse $\tilde{A}^{-1}$ of the matrix A and consequently an estimate $\hat{d}$ of d by $\hat{d} = \tilde{A}^{-1} \cdot c$.

The numerous methods for obtaining a pseudo-inverse for the matrix A include the conventional non-parametric methods based on the truncation of the singular values of A such as sSVD (simple Singular Value Decomposition), cSVD (circular Singular Value Decomposition) and oSVD (oscillation Index Singular Value Decomposition).

The sSVD method has the advantage of being simple and quick. Nevertheless, it suffers from two major drawbacks:

It is sensitive to the time delay $\tau$ between the arterial input function $C_a(t)$ and the concentration curve C(t), that is to say that it supplies estimates of parameters such as BF and MTT which depend on $\tau$ although they do not have to;

iI particular, it supplies estimates of the aberrant parameters when said time delay $\tau$ is negative, that is to say when the arterial input function $C_a(t)$ is delayed with respect to the concentration curve C(t).

These drawbacks are remedied by the cSVD and oSVD methods which by construction are insensitive to the time delay $\tau$ and make it possible to take account of the negative time delays.

The cSVD method (as well as the sSVD method) nevertheless suffers from a considerable drawback: it is not adaptive. Indeed the regularisation is predetermined once for all with the aid of a PSVD parameter specific to the algorithm which may be interpreted as the cutoff frequency of a low-pass filter. On the other hand the regularisation should adapt to each experimental concentration curve C(t), in particular the signal-to-noise ratio thereof. In practice, therefore, a value of the parameter PSVD should be determined beforehand which is adapted to each set of perfusion data of interest by determining for example the value enabling optimisation of a given criterion (e.g. the relative error on a parameter, etc.). This is stricto sensu impossible since the theoretical values of the parameters are not known. Of the second part, a such calibration in order to each mode of perfusion (e.g. On the other hand, such a calibration for each mode of perfusion (e.g. CT perfusion or MR PWI), each measuring apparatus, each set of acquisition parameters and even each type of perfusion signals (e.g. perfusion in the white matter, in the grey matter, healthy or pathological perfusion) is clearly not desirable. In practice, these calibrations are rarely performed and the parameter PSVD is often fixed in a quite arbitrary manner.

The oSVD method makes it possible to remedy this drawback to some extent by introducing a semi-adaptive regularisation, which renders/returns it less sensitive to the different experimental conditions and to the different types of perfusion signals. This method is, by construction, invariant by time period and semi-adaptive. Consequently, the oSVD method is supposed to provide estimates of haemodynamic parameters which are of better quality and more robust with respect to the operating conditions which the cSVD and sSVD methods do not do.

On the other hand, the implementation of such a method is complex and not sufficiently documented—as evidenced, for example and in an imperfect or erroneous manner, by the document WO2005/009204A2—in order to render it applicable effectively in a hospital environment. The same applies to the cSVD method. At present oSVD and cSVD remain theoretical. Furthermore, as we shall see below, the complexity algorithmic of oSVD may be of the order of N times that of cSVD and 4N times that of sSVD. If the calculation time for typical data sets of perfusion imaging with conventional calculation equipment (i.e. personal computer or work station) are of the order of several seconds for the sSVD and cSVD methods, they can therefore reach several minutes with the oSVD method. This is absolutely prohibitive in a clinical emergency situation, such as for example during the treatment of strokes where it is estimated that 4 million neurons die each minute.

The present invention consists, according to a first object, of implementing the oSVD method in order to be able to use it in a medical imaging system. The invention likewise relates to an embodiment particularly optimised from the point of view of the short time necessary for estimation of a quantity of interest. The invention is illustrated preferably—but in a non-limiting manner—in association with the use of a medical imaging system in order to estimate one or several quantities of interest (or haemodynamic parameters) by perfusion imaging. The optimised mode of implementation produces an algorithmic complexity of the same order as that of the cSVD method. Consequently calculation times for the oSVD according to the invention are obtained which are of the order of several seconds with conventional calculation equipment, acceptable in a clinical emergency situation.

According to a second object, the invention makes it possible to apply an equivalent approach in order to favour the implementation of the cSVD method.

To this end, a first embodiment is provided of a method implemented by a processing unit of a medical imaging analysis system for producing an estimate of a haemodynamic parameter on the basis of experimental intensity signals S(t), said estimation being carried out on the basis of an estimate $\hat{d}$ of a quantity of interest d of a dynamic artery/tissue/vein system of an elementary volume—referred to as a voxel—of an organ. Said estimate consists of calculating $\hat{d}=\tilde{A}^{-1} \cdot c$, $\tilde{A}^{-1}$ being a pseudo-inverse of a convolution matrix A and c describing a concentration of a contrast agent in said voxel, said concentration curve resulting from a prior conversion of said experimental signals. According to this first embodiment, the method includes:

a step for breaking down A canonically to singular values in the form $A=U \cdot S \cdot V^T$ where $S \equiv \mathrm{diag}(\sigma_1, \ldots, \sigma_L)$ is the diagonal matrix of singular values classified by increasing order, $V^T$ is the transpose of a matrix V, $V=(v_{ij})$ and $U=(u_{ij})$ are two unitary and real square matrices of dimension L×L, L≥N, N being a defined number of samples, $\hat{d}$, A and c respectively having dimensions L×1, L×L and L×1;

at least one step for:
producing a pseudo-inverse of $\tilde{A}_l^{-1}$ of A, in the form $\tilde{A}_l^{-1}=V \cdot W_l \cdot U^T$, $U^T$ designating the transpose of U with $$W_l = \mathrm{diag}\!\left(\underbrace{0,\ldots,0}_{l}, 1/\sigma_{l+1}, \ldots, 1/\sigma_L\right)$$

$0 < l \le L$;

producing $d_l = \tilde{A}_l^{-1} \cdot c$.

at least one step for producing the estimate of the haemodynamic parameter on the basis of the estimate of the quantity of interest $\hat{d}=d_{l_F}$ produced with the iteration $l_F$, $l_F$ being positive and less than or equal to L.

The invention provides a variant in order to improve the performance for carrying out such a method since $\tilde{A}_l^{-1}$ does not depend upon the concentration curves. Thus for any voxel Vi of interest, the iterative step for producing $\tilde{A}_l^{-1}$, $0 < l \le L$, may be carried out once for all after the step where A is broken down canonically into singular values.

The invention advantageously provides that the method can include, prior to each step in order to produce $d_l$, the verification of a regularisation condition, said method being interrupted with the iteration $l_F$ as soon as said condition is met, the estimate of d being $\hat{d}=d_{l_F}$. By way of preferred example, the regularisation condition may consist of the calculation an oscillation index $OI_l$, said regularisation condition being met as soon as $OI_{l_F} \le POI$, POI being a sole predetermined value.

In order to respond to clinical emergency situations, the invention provides a second embodiment optimised from the point of view of the calculation time in order to produce an estimate of a haemodynamic parameter on the basis of experimental intensity signals S(t), said estimate being carried out on the basis of an estimate $\hat{d}$ of a quantity of interest d of a dynamic artery/tissue/vein system of an elementary volume—referred to as a voxel—of an organ. Like the previous method, this one is implemented by a processing unit of a medical imaging analysis system, said estimation consisting of calculating $\hat{d}=\tilde{A}^{-1} \cdot c$, $\tilde{A}^{-1}$ being a pseudo-inverse of a convolution matrix A and c describing a concentration of a contrast agent in said voxel, said concentration curve resulting from a prior conversion of said experimental signals. According to the invention, the method still includes a first step for breaking down A canonically into singular values in the form $A=U \cdot S \cdot V^T$ where $S \equiv \mathrm{diag}(\sigma_1, \ldots, \sigma_L)$ is the diagonal matrix of positive singular values classified by increasing order, $V^T$ is the transpose of a matrix V, $V=(v_{ij})$ and $U=(u_{ij})$ are two unitary and real square matrices of dimension L×L, L≥N, N being a defined number of samples, $\hat{d}$, A and c respectively having dimensions L×1, L×L and L×1.

On the other hand, such a method also includes:
prior to each step for producing $d_l$, the verification of a regularisation condition consisting of the calculation an oscillation index $OI_l$, said regularisation condition being met as soon as $OI_{l_F} \le POI$, POI being a predetermined threshold value, said method being interrupted with the iteration $l_F$ as soon as said condition is met;

a step for producing the estimate of the haemodynamic parameter on the basis of the estimate of the quantity of interest $\hat{d}=d_{l_F}$ produced with the iteration $l_F$, $l_F$ being strictly positive and less than or equal to L.

Such an oscillation index may be calculated such as $$OI_l \equiv \frac{1}{L} \frac{1}{\max\limits_{i=1,L} d_l(i)} \sum_{i=3}^{L} |d_l(i) - 2d_l(i-1) + d_l(i-2)|,$$

or as a variant, such as $$OI_l \equiv \frac{1}{\Delta t^2 \cdot L} \frac{1}{\max\limits_{i=1,L} d_l(i)} \sum_{i=3}^{L} |d_l(i) - 2d_l(i-1) + d_l(i-2)|,$$

where $\Delta t$ is the sampling period of the signals S(t).

Regardless of the chosen embodiment according to the invention, in order to initialise the iterative step, a method according to the invention can include an initial step for producing $d_0 = A_{l=0}^{-1} \cdot c$.

The convolution matrix A may advantageously be block-circulant with dimension L×L defined by $$A = \Delta t \cdot \begin{pmatrix} C_a(t_1) & 0 & \cdots & C_a(t_N) & \cdots & C_a(t_2) \\ \vdots & C_a(t_1) & & & \ddots & \vdots \\ C_a(t_N) & & \ddots & & & C_a(t_N) \\ 0 & \ddots & & \ddots & & 0 \\ \vdots & \ddots & \ddots & & \ddots & \vdots \\ 0 & \cdots & 0 & C_a(t_N) & \cdots & C_a(t_1) \end{pmatrix},$$

$\Delta t$ being the sampling period, $C_a(t)$ being a concentration of the contrast agent.

In order to implement a method according to the invention, the invention likewise provides a processing unit including memory means, means for communicating with the outside world and processing means. The means for communicating are capable of receiving from the outside world an experimental data item c describing a concentration curve of a contrast agent in an elementary volume—referred to as a voxel—of an organ and the processing means are adapted in order to implement a method for producing an estimate of a haemodynamic parameter according to the invention.

Preferably, the communication means of such a processing unit may deliver an estimated quantity of interest $\hat{d}$ in a format appropriate to a men-machine interface suitable for returning it to a user.

If the implemented method makes it possible according to the invention to produce the estimate of a haemodynamic parameter, such a processing unit may be adapted to deliver said estimate—in an appropriate format—to a human-machine interface suitable for returning it to a user.

The invention also relates to any medical imaging analysis system which includes a processing unit adapted in accordance with the invention and a men-machine interface suitable for returning to a user an estimated quantity according to a method according to the invention and implemented by said processing unit.

Other characteristics and advantages will become clearer by reading the following description and studying the drawings accompanying it, in which:

FIGS. 1 and 2, partially previously described, show two variants of implementation of a medical imaging analysis system;

Figure 1:
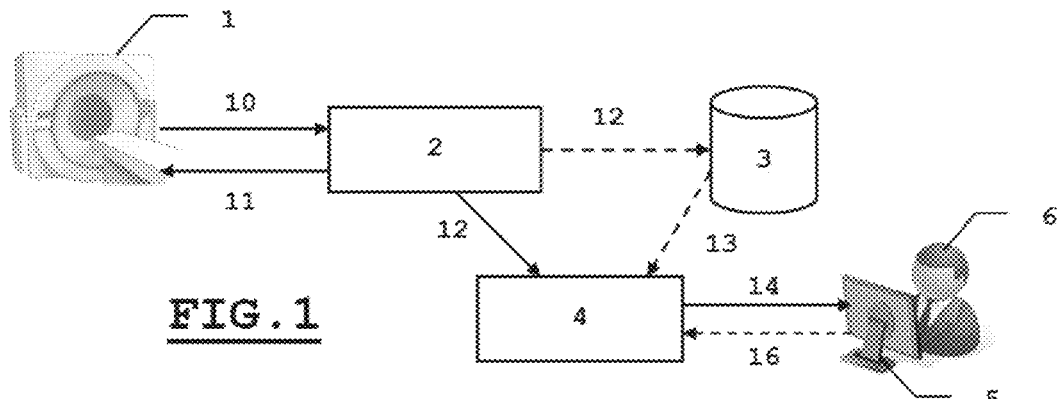

In a more detailed manner, FIG. 1 makes it possible to show a medical image analysis system. An apparatus 1 for imaging by nuclear magnetic resonance or by computed tomography is controlled with the aid of a console 2. Thus a user can choose parameters 11 in order to control the apparatus 1. On the basis of information 10 produced by the apparatus 1, a plurality of digital image sequences 12 of a part of a body of a human or an animal. By way of example preferred, we will illustrate the solutions disclosed by the prior art as well as the invention with the aid of digital images resulting from the observation of a human brain. Other organs could also be considered.

The sequences of images 12 may optionally be stored within a server 3 and constitute a patient's medical file 13. Such a file 13 may comprise images of different types, such as perfusion-weighted or diffusion-weighted images. The sequences of images 12 are analysed by means of a dedicated processing unit 4. Said processing unit includes means for communicating with the outside world for collection of the images. Said communication means also make it possible for the processing unit to ultimately deliver to a practitioner 6 or to a researcher an estimate of haemodynamic parameters 14 on the basis of perfusion-weighted images, by means of an adapted men-machine interface 5. Thus the user 6 of the analysis system can thus confirm or refute a diagnosis, decide upon a therapeutic action which he considers suitable, conduct research work in greater depth . . . . Optionally, this user may parameterise the operation of the processing unit 4 by means of parameters 16. For example, he may thus define display thresholds or choose the estimated parameters which he wishes to display.

Figure 2:
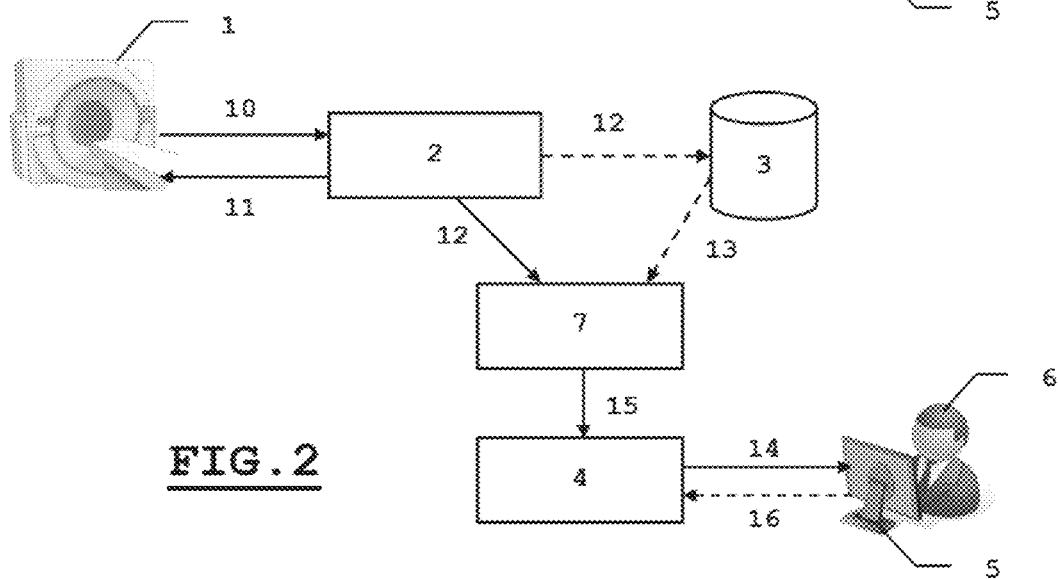

FIG. 2 illustrates an alternative embodiment of an analysis system for which a pre-processing unit 7 analyses sequences of images 12 in order to deduce perfusion data 15 therefrom by voxel. Thus this processing unit 4 responsible for estimating the haemodynamic parameters 14 is relieved of responsibility for this action and implements a method of estimation on the basis of perfusion data 15 received by its means for communication with the outside world.

Figure 3:
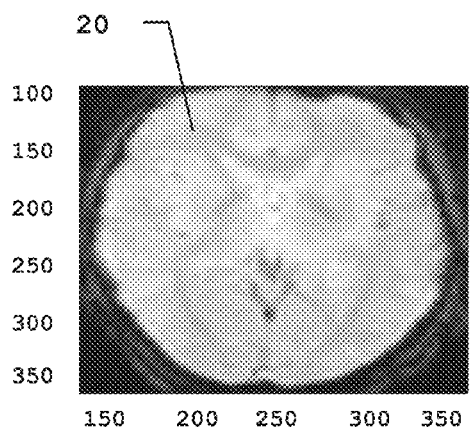
FIGS. 3 and 4 show respectively an image of perfusion, obtained by a nuclear magnetic resonance imaging apparatus, of a slice of a human brain before the injection of a contrast agent and during the circulation thereof in the tissue of said brain.

FIG. 3 illustrates an example of a typical image 12 of a slice 5 millimeters thick of a human brain. This image is obtained by nuclear magnetic resonance. With the aid of this technique, it is possible to obtain, for each slice, a matrix of 128×128 voxel of which the dimensions are 1.5×1.5×5 millimeters. With the aid of a bilinear interpolation it is possible to produce a flat image of 458×458 pixels such as the image 20.

Figure 4:
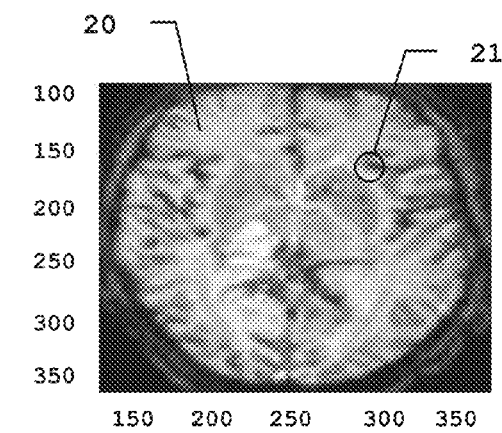

FIG. 4 illustrates an image 20 similar to that presented in connection with FIG. 3. However, this image is obtained after an injection of a contrast agent. This image is an example of a typical image of perfusion of a brain. Thus the arteries appear clearly contrary to the same image described in FIG. 3. According to known techniques, it is possible to choose one or several arterial input functions 21 in the hemisphere contralateral to the pathological hemisphere in order to estimate haemodynamic parameters.

Figure 5A:
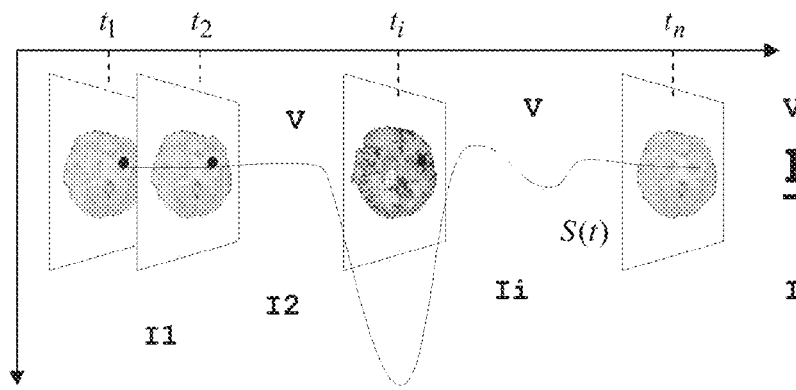
FIGS. 5a and 5b show a typical perfusion signal S(t) by nuclear magnetic resonance typical relating to a voxel of a human brain.
Figure 5B:
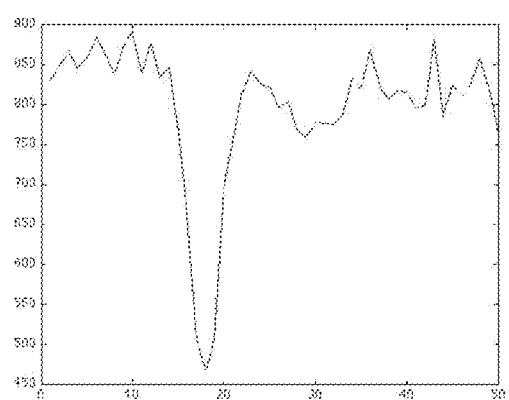

FIG. 5b makes it possible to illustrate an example of a perfusion-weighted signal S(t) by nuclear magnetic resonance such as the data 15 delivered by the pre-processing unit 7 describes in connection with FIG. 2. Thus the perfusion-weighted signal is representative of the development of a voxel over the time t following an injection of a contrast agent. By way of example, FIG. 5b describes such a signal over a period of 50 seconds. The ordinate describes the intensity of the signal in arbitrary units. In order to obtain such a signal, the processing unit 4 according to FIG. 1 (or as a variant the pre-processing unit 7 according to FIG. 2), analyses a sequence of n perfusion-weighted images by nuclear magnetic resonance I1, I2, . . . , Ii, . . . , In at time points $t_1$, $t_2, \ldots, t_i, \ldots, t_n$ as described for example in FIG. 5a. Thus for a given voxel, for example the voxel V, a perfusion-weighted signal S(t) is determined which is representative of the evolution of the voxel over time t following an injection of a contrast agent.

Figure 6:
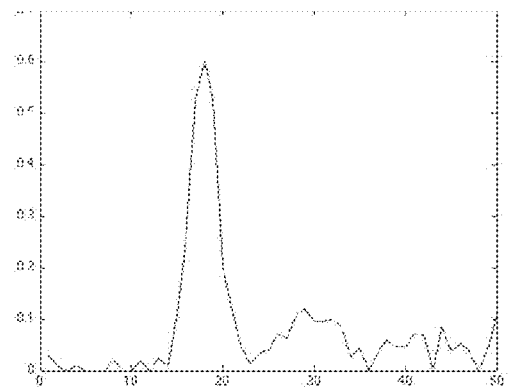
FIG. 6 shows a typical concentration curve C(t) of a contrast agent circulating within a voxel of a human brain.

FIG. 6 shows a concentration curve deduced from a perfusion-weighted signal such as that described in FIG. 5b. As already mentioned previously, there is a relationship between a perfusion-weighted signal and an associated concentration curve. Thus in perfusion-weighted nuclear resonance magnetic imaging there is an exponential relationship $S(t) = S_0 \cdot e^{-k \cdot TE \cdot C(t)}$, where $S_0$ is the average intensity of the signal before the arrival of the contrast agent, TE is the echo time and k is a constant depending upon the relationship between the paramagnetic susceptibility and the concentration of the contrast agent in the tissue.

Thus FIG. 6 makes it possible to view the evolution of the concentration of a contrast agent within a voxel over time. A high amplitude peak is noted during the first pass of the contrast agent in the voxel followed by lower amplitude peaks linked to the phenomenon of recirculation (second pass) of said contrast agent.

Figure 7:
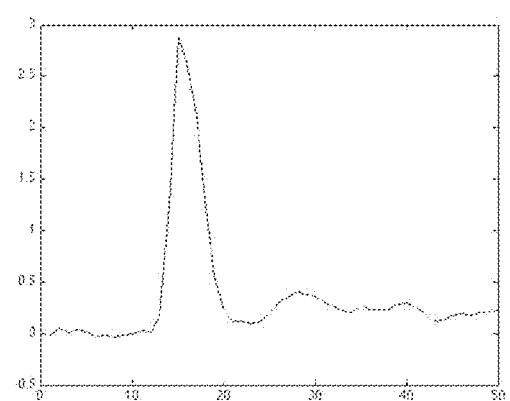
FIG. 7 shows a typical arterial input function $C_a(t)$.

On the other hand, FIG. 7 illustrates a typical arterial input function $C_a(t)$ representing of the circulation of a contrast agent within an arterial voxel such as the voxel 21 presented in connection with FIG. 4. FIG. 7 makes it possible to note in particular that the phenomenon of recirculation after a first pass of the contrast agent is very weak.

Figure 8:
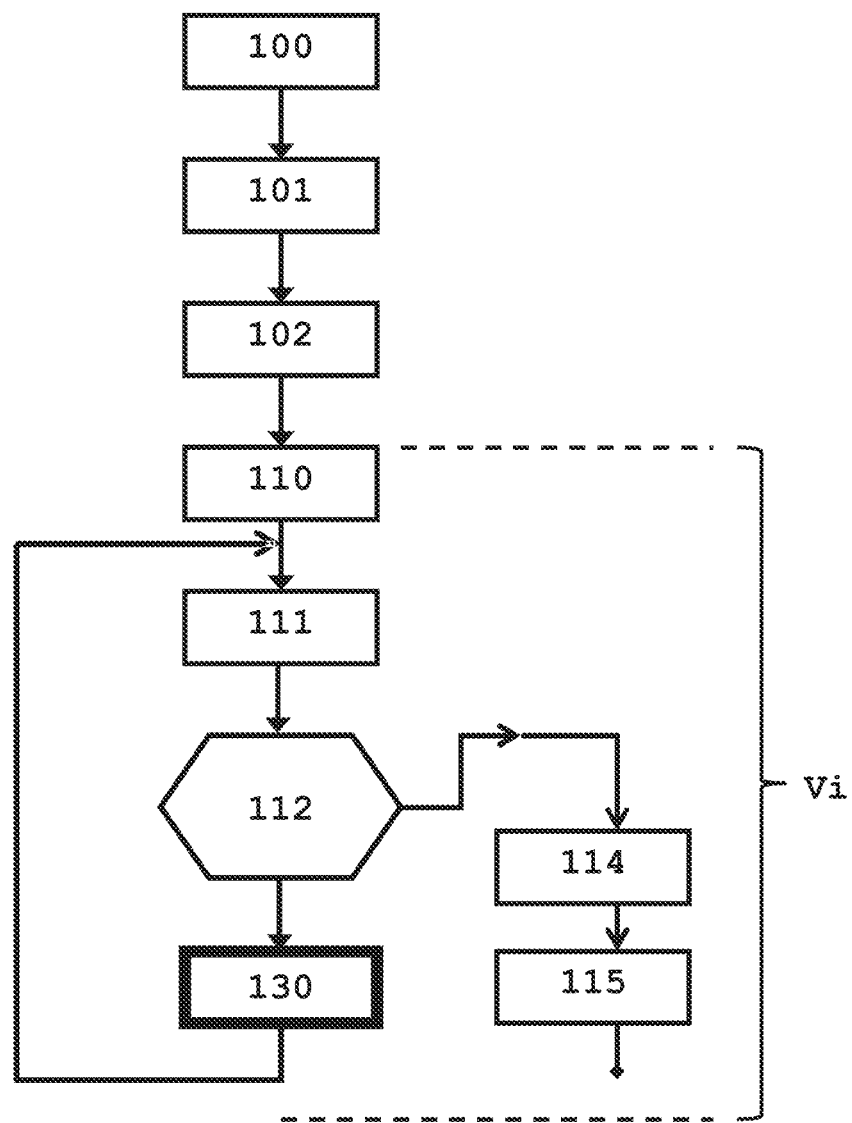
FIGS. 8 and 9 show methods according to the invention in order to implement the oSVD method.

FIG. 8 makes it possible to describe an implementation according to the invention of the oSVD method. This implementation is preferably applied to perfusion-weighted imaging.

A method for estimating a quantity of interest may include a first initial step 100 in order to select an arterial input function $C_a(t)$.

According to the oSVD method, the standard model of the perfusion is discretised temporally at the measurement time points in the form of a linear system $C = A \cdot d$ with:

$$A = \Delta t \cdot \begin{pmatrix} C_a(t_1) & 0 & \ldots & C_a(t_N) & \ldots & C_a(t_2) \\ \vdots & C_a(t_1) & & & \ddots & \vdots \\ C_a(t_N) & & \ddots & & & C_a(t_N) \\ 0 & \ddots & & \ddots & & 0 \\ \vdots & \ddots & \ddots & & \ddots & \vdots \\ 0 & \ldots & 0 & C_a(t_N) & \ldots & C_a(t_1) \end{pmatrix},$$

$$b = \begin{vmatrix} R(t_1) \\ \vdots \\ R(t_N) \\ 0 \\ \vdots \\ 0 \end{vmatrix},$$

$$c = \begin{vmatrix} C(t_1) \\ \vdots \\ C(t_N) \\ 0 \\ \vdots \\ 0 \end{vmatrix}$$

and $d = BF \cdot b$.

A, b, c and d are respective dimensions L×L, L×1, L×1 and L×1 with L≥N. In the following, $v(i)$, $i=1,L$ denotes the components of a vector v of dimension L. In the case where L≥2N−1, the implementation makes it possible to estimate both negative and positive time delays/TMAX.

Thus a step 101 consists of constructing the circular block-circulant convolution matrix A.

According to the invention, the circular block-circulant convolution matrix A is first of all—in 102—broken down canonically into singular values in the form $A = U \cdot S \cdot V^T$ where $S = \text{diag}(\sigma_1, \ldots, \sigma_L)$ is the diagonal matrix of the positive singular values classified for example by increasing order (i.e. $\sigma_1 \leq \sigma_2 \leq \ldots \leq \sigma_L$), $U \equiv (u_{ij})$ and $V \equiv (v_{ij})$ are two unitary real square matrices L×L and $V^T$ designates here the transpose of V.

For any voxel V of interest, a method according to the invention consists of implementing an iterative step 130 in order to produce an estimate $\hat{d}$ of a quantity of interest d. This production is preferably carried out as long as a regularisation condition 112 is not verified. For this, a criterion such as an oscillation index $OI_l$, is calculated in advance in 111 and with each iteration l. By way of preferred example, said regularisation condition is met as soon as $OI_l$ is greater than or equal to a given strictly positive predefined value POI. The iteration of the step 130 stops as soon as said condition is met with the iteration $l_F$. Consequently such a method considers, in 114, that the estimate $\hat{d}$ is $d_{l_F}$.

According to the invention, it becomes possible to produce in 115, for example and respectively, estimates of haemodynamic parameters BF, MTT, BV, or else of the vector b by $$\max_{i=1,L} d_{l_F}(i),$$

$$\frac{\Delta t}{\max_{i=1,L} d_{l_F}(i)} \cdot \sum_{i=1}^{L} d_{l_F}(i),$$

$$\Delta t \cdot \sum_{i=1}^{L} d_{l_F}(i)$$

and $$\frac{d_{l_F}}{\max_{i=1,L} d_{l_F}(i)}.$$

Likewise, according to the invention it becomes possible to produce estimates of TMAX, for example, by $$TMAX = \Delta t \cdot \operatorname*{argmax}_{i=1,L} d_{l_F}(i) \quad \text{if } L = N \text{ or}$$

$$TMAX = \begin{cases} \delta t \cdot \operatorname*{argmax}_{i=1,L} d_{l_F}(i) & \left( \text{if } \operatorname*{argmax}_{i=1,L} d_{l_F}(i) < L/2 \right) \\ -\Delta t \cdot \left( L - \operatorname*{argmax}_{i=1,L} d_{l_F}(i) \right) & \left( i \operatorname*{argmax}_{i=1,L} d_{l_F}(i) \geq L/2 \right) \end{cases}$$

if L≥2N−1, where $\Delta t$ is the sampling period of the signals $S(t)$.

In order to implement the iteration or iterations necessary for the production of the quantity of interest, the invention provides a step 110 in order to initialise any parameter necessary for said production.

According to a first embodiment according to the invention and described in connection with FIGS. 8 and 9, the production 130 of the quantity of interest d consists of two sub-steps 131 and 132. Thus, in 131 with the iteration l a pseudo-inverse $\tilde{A}_l^{-1}$ of A is produced in the form $\tilde{A}_l^{-1} = V \cdot W_l \cdot U^T$ where the diagonal matrix $W_l \equiv \text{diag}(w_l, \ldots, w_L)$ is itself obtained by proceeding by successive iterations in the following manner. With the first iteration (l=0): $W_0 = S^{-1} = \text{diag}(1/\sigma_1, \ldots, 1/\sigma_L)$.

During a subsequent possible iteration (l=1), the matrix W is obtained by cancelling the first diagonal coefficient $w_1 = 1/\sigma_1$ of the matrix $W_0$ such as $W_1 = \text{diag}(0.1/\sigma_2, \ldots, 1/\sigma_L)$ and so forth by cancelling each time the diagonal coefficient $w_l$ of the matrix $W_{l-1}$ until the regularisation condition $OI_{l_F} \leq POI$ is met with the iteration $l = l_F$. Therefore $W \equiv W_{l_F}$.

The step 131 then makes it possible to produce the pseudo-inverse $Al = V \cdot W \cdot U^T$ then $d = BF \cdot b$ by $d_l = \tilde{A}_l^{-1} \cdot c$ is calculated in 132.

The oscillation index $OI_l$ may consist of:

$$OI_l \equiv \frac{1}{L} \frac{1}{\max_{i=1,L} d_l(i)} \sum_{i=3}^{L} |d_l(i) - 2d_l(i-1) + d_l(i-2)|$$

or as a variant, such as $$OI_l \equiv \frac{1}{\Delta t^2 \cdot L} \frac{1}{\max_{i=1,L} d_l(i)} \sum_{i=3}^{L} |d_l(i) - 2d_l(i-1) + d_l(i-2)|$$

where $\Delta t$ is the sampling period of the signals $S(t)$.

This first embodiment of the oSVD method, which we will designate as "direct", therefore consists of calculating the double matrix product $\tilde{A}_l^{-1} = V \cdot W_l \cdot U^T$ then the matrix-vector product $d_l = \tilde{A}^{-1} \cdot c$ with each iteration l of the algorithm until the regularisation condition OI≤POI is met.

Advantageously, as a variant provision may be made for pre-calculation once for all of all the pseudo-inverses $\tilde{A}_l^{-1}$, l=0,L−1 which are only dependent upon the arterial input function and not on the concentration curves. According to this variant, the step 131 is carried out prior to all those implemented for a voxel $V_o$ of interest, for example at the end of the step 102 where A is broken down canonically into singular values.

It may be noted, including the implementation of this variant which makes it possible to ignore the impact of the step of pre-calculation of the pseudo-inverses $\tilde{A}_l^{-1}$ in relation to the processing of all the voxels of interest, that considering that the number $l_F$ of iterations necessary in order to meet the regularisation condition $OI_{l_F} \leq POI$ is of the order of N, the implementation of the oSVD method therefore has an algorithmic complexity a priori of the order of $O(L^2 \cdot N) = O(4N^3)$ for each voxel of interest, since the matrix-vector multiplications $d_l = \tilde{A}_l^{-1} \cdot c$ each require $O(L^2)$ operations.

In particular, the complexity of such a method according to the invention is of the order of N times that of an algorithm in order to implement the cSVD and 4N times that of an algorithm in order to implement the sSVD. The number of measurements N being typically between 40 (e.g. in CT perfusion) and 70 (e.g. in MR PWI), the algorithm oSVD is considerably slower than the algorithms cSVD and sSVD.

Consequently, as it is invariant by time period and semi-adaptive, the oSVD method supplies estimates of the haemodynamic parameters which are of better quality and more robust with respect to the operating conditions which the cSVD and sSVD methods do not do. This is therefore preferable if the calculation time is not a paramount criterion.

In an emergency situation, such an implementation time in order to produce an estimate of a quantity of interest may be prohibitive.

It will be recalled that the cost of conventional calculation equipment is typically proportional to their power: a machine 50 times more powerful typically costs 50 times more, such that it is not economically viable to resort to more powerful conventional hardware in order to obtain acceptable calculation times for the oSVD method in a clinical emergency situation. Indeed, it is possible to envisage less expensive dedicated calculation equipment, e.g. graphics cards, FPGA (field programmable gate array) cards, but by definition such dedicated equipment solutions can be costly to develop and have a limited applicability.

The present invention also consists of fast implementation of the oSVD method, with an algorithmic complexity of the same order as that of the cSVD method. Thus the invention makes it possible to obtain calculation times for the oSVD which are of the order of several seconds with conventional calculation equipment, acceptable in a clinical emergency situation. Such a method according to a second embodiment is illustrated in connection with FIG. 8. Such a method adopts the steps of a method according to the first embodiment. The step 130 is different in principle. In 102, the matrix A is still broken down canonically into singular values in the form $A = U \cdot S \cdot V^T$ where $S = \text{diag}(\sigma_1, \ldots, \sigma_L)$ is the diagonal matrix of the positive singular values. These are at present advantageously classified by increasing order (i.e. $\sigma_1 \leq \sigma_2 \leq \ldots \leq \sigma_L$).

The principle of this second embodiment consists of avoiding having to pre-calculate (step(s) 131 for the first embodiment) the matrices $\tilde{A}_l^{-1}$ and above all the matrix-vector products $d_l = \tilde{A}_l^{-1} \cdot c$ (in 132 according to the preceding embodiment) during each iteration of the algorithm. We will examine how this becomes possible according to this second embodiment.

With the iteration l>0 of a process according to the first embodiment such as described previously, we therefore have $$W_l = \text{diag}(\underbrace{0, \ldots, 0}_{l}, w_{l+1}, \ldots, w_L)$$

such that $$W_l \cdot U^T = \begin{pmatrix} 0 & \cdots & \cdots & 0 \\ \vdots & & & \vdots \\ 0 & \cdots & \cdots & 0 \\ w_{l+1}u_{1,l+1} & \cdots & \cdots & w_{l+1}u_{L,l+1} \\ \vdots & & & \vdots \\ w_L u_{1,L} & \cdots & \cdots & w_L u_{L,L} \end{pmatrix} \begin{matrix} 1 \\ \vdots \\ l \\ l+1 \\ \vdots \\ L \end{matrix}$$

By denoting $a_{ij}^l$ the coefficients of the matrix $\tilde{A}_l^{-1} = V \cdot W_l \cdot U^T$, we therefore have by definition $$a_{ij}^l = \sum_{k=l+1}^{L} v_{ik} w_k u_{jk}.$$

The i-th coefficient $d_l(i)$ of the vector $d_l = \tilde{A}_l^{-1} \cdot c$ is then written as $$d_l(i) = \sum_{j=1}^{N} a_{ij}^l \cdot c_j = \sum_{j=1}^{N} c_j \cdot \sum_{k=l+1}^{L} v_{ik} w_k u_{jk}$$

since $c_j = 0$ if $N < j \leq L$.

It is then possible to write:

$$d_{l-1}(i) = \sum_{j=1}^{N} c_j \cdot \sum_{k=l}^{L} v_{ik} w_k u_{jk}$$

$$= \sum_{j=1}^{N} c_j \cdot \left( \sum_{k=l+1}^{L} v_{ik} w_k u_{jk} + v_{il} w_l u_{jl} \right)$$

$$= d_l(i) + \sum_{j=1}^{N} c_j \cdot v_{il} w_l u_{jl}$$

in such a way as to obtain the first order recurrence formula $$d_l(i) = d_{l-1}(i) - \frac{v_{il}}{\sigma_l} \sum_{j=1}^{N} c_j \cdot u_{jl}$$

It will be noted therefore that it is possible to express the vector $d_l$ directly on the basis of vector $d_{l-1}$ obtained with the preceding iteration of the algorithm oSVD without having to perform any matrix operation but only by calculating one single sum $$\sum_{j=1}^{N} c_j \cdot u_{jl}.$$

By means of this recurrence formula implemented in the step 130 of a method according to that described in connection with FIG. 8, there is a change from an algorithmic complexity for each voxel of interest $V_i$ of the order of $O(L^2 \times N)$ according to the direct implementation to an algorithmic complexity of the order of $O(L^2 + L \times N)$ since it is necessary to initialise—step 110—the algorithm by calculating $d_0 = A^{-1}$ of complexity $O(L^2)$.

Therefore the supplementary cost in calculation time of this implementation with respect to the algorithm cSVD is no more than of the order of $O(L \times N) = O(2N^2)$, by comparison with the algorithmic complexity of the cSVD itself in $O(L^2) = O(4N^2)$. In practice, this second mode of fast or optimised implementation of the oSVD method is slower than the algorithm cSVD only by a factor 2 or 3 instead of a factor of the order of N according to the direct implementation conforming to the previously described first mode of implementation.

The calculations can therefore be performed once again in several seconds on conventional equipment. Thus the invention makes it possible to use the oSVD method for the estimation of haemodynamic parameters by perfusion-weighted imaging (for example) on conventional calculation equipment in a clinical emergency situation.

Figure 8B:
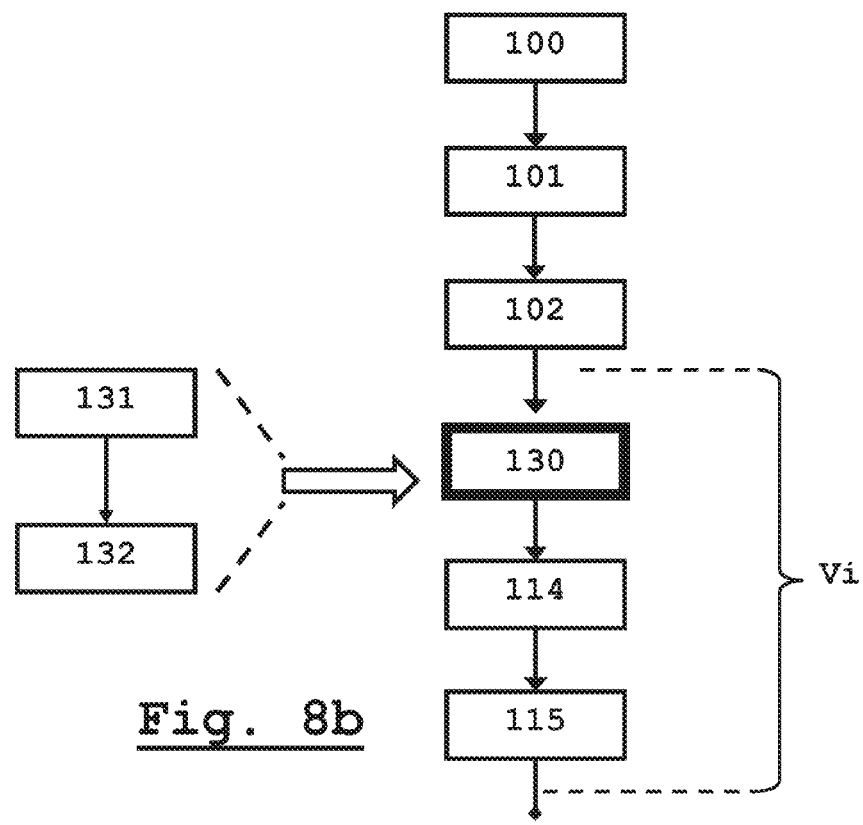
FIG. 8b shows a method according to the invention in order to implement the cSVD method.

A process according to the invention makes it possible to implement the method cSVD by a mode of operation similar to the first embodiment of a method according to the invention in order to implement the oSVD method. FIG. 8b illustrates such a method applied to the cSVD method.

Figure 9:
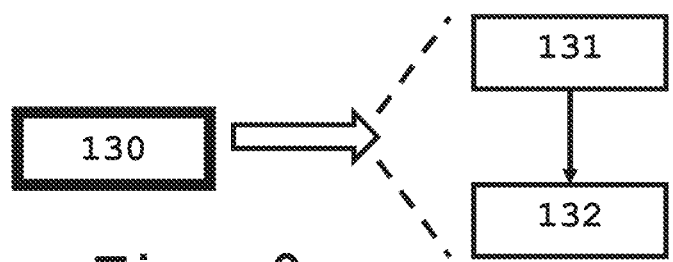

Thus, like a method according to FIGS. 8 and 9, a method according to the invention for implementing the cSVD method includes a first step 100 for selection of an arterial input function $C_a(t)$.

According to the cSVD method, the standard model of the perfusion is also discretised temporally at the measurement time points in the form of a linear system $C = A \cdot d$ with:

$$A = \Delta t \cdot \begin{pmatrix} C_a(t_1) & 0 & \dots & C_a(t_N) & \dots & C_a(t_2) \\ \vdots & C_a(t_1) & & & \ddots & \vdots \\ C_a(t_N) & & \ddots & & & C_a(t_N) \\ 0 & & & \ddots & & 0 \\ \vdots & \ddots & \ddots & & \ddots & \vdots \\ 0 & \dots & 0 & C_a(t_N) & \dots & C_a(t_1) \end{pmatrix},$$

$$b = \begin{vmatrix} R(t_1) \\ \vdots \\ R(t_N) \\ 0 \\ \vdots \\ 0 \end{vmatrix}, \quad c = \begin{vmatrix} C(t_1) \\ \vdots \\ C(t_N) \\ 0 \\ \vdots \\ 0 \end{vmatrix}$$

and $d = BF \cdot b$.

A, b, c and d are respective dimensions $L \times L$, $L \times 1$, $L \times 1$ and $L \times 1$ with $L > N$.

Thus a step 101 consists of constructing the circular block-circulant convolution matrix A.

According to the invention, the circular block-circulant convolution matrix A is first of all—in 102—broken down canonically into singular values in the form $A = U \cdot S \cdot V^T$ where $S = \mathrm{diag}(\sigma_1, \ldots, \sigma_L)$ is the diagonal matrix of the positive singular values classified by increasing order (i.e. $\sigma_1 \leq \sigma_2 \leq \ldots \leq \sigma_L$), $U \equiv (u_{ij})$ and $V \equiv (v_{ij})$ are two unitary real square matrices $L \times L$ and $V^T$ designates here the transpose of V.

For any voxel $V_i$ of interest, a method according to the invention consists of implementing a step 130 in order to ultimately produce $d_{l_F}$ an estimate $\hat{d} = d_{l_F}$ in 114 of a quantity of interest d.

In the case of the cSVD method, this production of $d_{l_F}$ is preferably carried out by fixing once for all an integer $l_F$ such that $0 \leq l_F < L$.

According to the invention, it becomes possible to produce in 115, for example and respectively, estimates of haemodynamic parameters BF, MTT, BV, or else of the vector b by $$\max_{i=1,L} d_{l_F}(i), \quad \frac{\Delta t}{\max_{i=1,L} d_{l_F}(i)} \cdot \sum_{i=1}^{L} d_{l_F}(i), \quad \Delta t \cdot \sum_{i=1}^{L} d_{l_F}(i) \text{ and}$$

$$\frac{d_{l_F}}{\max_{i=1,L} d_{l_F}(i)}.$$

The invention described in connection with FIG. 8 the production 130 of the quantity of interest d consists of two sub-steps 131 and 132. Thus in the case of the cSVD, in 131 a pseudo-inverse $\tilde{A}_{l_F}^{-1}$ of A is produced in the form $\tilde{A}_{l_F}^{-1} = V \cdot W_{l_F} \cdot U$ where the diagonal matrix $W_{l_F}$ is such that $$W_{l_F} = \mathrm{diag}\bigl(\underbrace{0, \ldots, 0}_{l_F}, w_{l_F+1}, \ldots, w_L\bigr),$$

the integer $0 < l_F < L$ being fixed once for all by the method, then in 132 $d_{l_F} = BF \cdot b$ by $d_{l_F} = \tilde{A}_{l_F}^{-1} \cdot c$ is calculated.

As a variant the invention also provides for pre-calculation once for all of all the pseudo-inverses $\tilde{A}_{l_F}^{-1}$ which are only dependent upon the arterial input function and not on the concentration curves. According to this variant, the step 131 is carried out prior to all those implemented for a voxel $V_i$ of interest, for example at the end of the step 102 where A is broken down canonically into singular values.

By way of an exemplary application, reference may be made to the main steps for implementation of the invention by means of an adapted medical imaging analysis system, such as that described in FIG. 1 or 2:

opening of a patient file or taking account of sequences of images by the processing unit 4 (or the pre-treatment unit 7) in order to select sequences of images of interest—in particular, selection of the perfusion-weighted images I1 to In over time on the basis of which the perfusion-weighted signals of S(t) are obtained for each voxel, as illustrated in FIG. 5a;

pre-visualisation by means of a men-machine interface 5 of the images in order to enable a user 6 to identify slices or zones of interest;

configuration of the processing unit 4 on the basis of configuration parameters (information introduced) in order to enable the implementation of the method of estimation according to the invention;

choice of the quantity or quantities of interest to be estimated;

estimation by the processing unit 4 of quantities of interest 14, such as the blood flow BF or MTT for an organ such as the human brain;

delivery of said estimated quantities of interest 14 to the men-machine interface 5 so that this latter ultimately shows them for example in the form of maps where the intensity or the colour of each pixel depends upon the calculated value in order to return the content to the practitioner.

The invention therefore provides for display of the estimates of parameters in the form of "parameter maps" where the intensity or the colour of each voxel depends upon the value calculated, for example in a linear manner.

Figure 11:
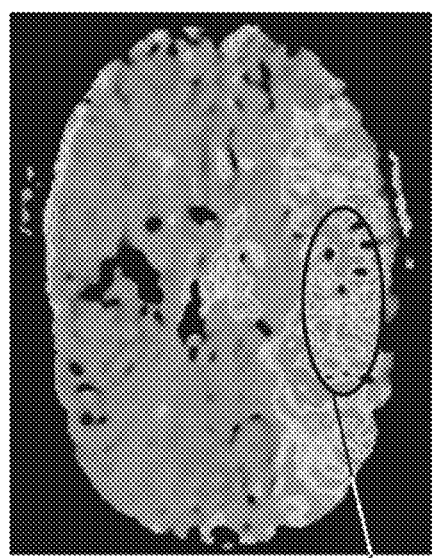
FIGS. 10 and 11 show respectively an example of a map relating to quantities of interest estimated in accordance with the invention.
Figure 10:
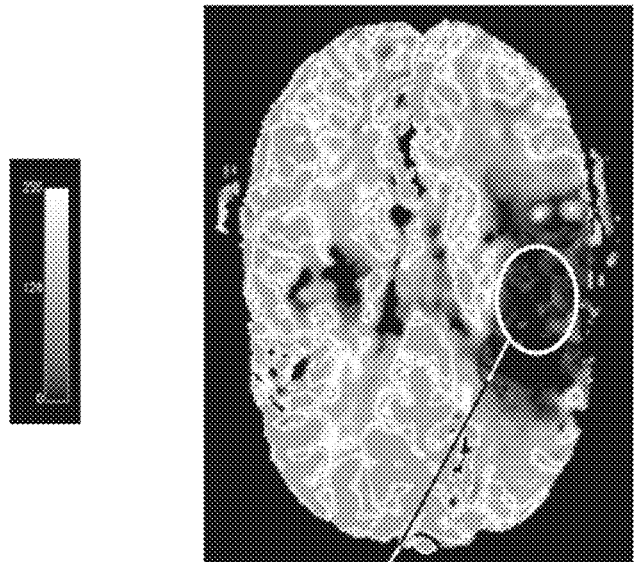

FIGS. 10 and 11 make it possible to illustrate a mode of display in the form of maps, of certain quantities of interest such as haemodynamic parameters 14 estimated in accordance with the invention.

Thus, for a human brain analysed with the aid of nuclear magnetic resonance imaging, FIG. 10 makes it possible to view an estimate of the blood flows. It shows a map (458×458 pixels) relating to cerebral blood flows—in the case of cerebral ischaemia—estimated in accordance with the invention. Such a map makes it possible to demonstrate a probable ischaemic zone 80.

FIG. 11 makes it possible to illustrate a map (458×458 pixels) relating to the estimation of the mean transit times MTT. By analysing the map, a clear increase in the MTT in the territory 81 of the right posterior cerebral artery with respect to the contralateral hemisphere following the ischaemia is shown.

The invention is not limited solely to the specific oSVD or cSVD methods as described previously. For example, the invention also applies to variants of the oSVD method, for example methods including stopping criteria different from the criterion OI≤POI described previously.

In general, the invention applies to any method of numerical deconvolution based on the adaptive truncation of a decomposition into singular values of a convolution matrix. For example, the invention may apply directly to any method based on the lower triangular Toeplitz convolution matrix described previously instead of the block-circulant convolution matrix of the cSVD and oSVD methods. Thus for example a method would be obtained for fast estimation of haemodynamic parameters by perfusion-weighted imaging which would be to the sSVD what the oSVD is to the cSVD and it would therefore be appropriate to call the method osSVD.

Finally, the invention does not apply only to perfusion-weighted imaging but to any type of data of which the processing is to be performed including in less time.

The invention claimed is:

1. A method implemented by a processing unit of a medical imaging analysis system for producing an estimate of a haemodynamic parameter in a dynamic artery/tissue/vein system, on the basis of experimental intensity signals S(t), wherein the method comprises:

obtaining a signal S(t), wherein said signal S(t) represents the evolution of a voxel of interest of a plurality of voxels over time t, wherein the plurality of voxels constitute elementary volumes of an organ;

deriving, from the signal S(t), a concentration curve c for the voxel of interest;

performing, by the processing unit, a step for breaking down a convolution matrix A canonically into singular values in the form $A = U \cdot S \cdot V^T$ where $S \equiv \mathrm{diag}(\sigma_1, \ldots, \sigma_L)$ is the diagonal matrix of positive singular values classified by increasing order, $V^T$ is the transpose of a matrix V, and $V=(v_{ij})$ and $U=(u_{ij})$ are two unitary and real square matrices of dimension L×L, L≥N, N being a defined number of samples, A and c respectively having dimensions L×L and L×1;

performing, by the processing unit, at least one iterative step for:

producing a pseudo-inverse $\tilde{A}_l^{-1}$ of A, in the form $\tilde{A}_l^{-1} = V \cdot W_l \cdot U^T$, where $U^T$ designates the transpose of U, and where $$W_l = \mathrm{diag}(\underbrace{0, \ldots, 0}_{l}, 1/\sigma_{l+1}, \ldots, 1/\sigma_L) \, 0 < l \leq L;$$

producing $d_l = \tilde{A}^{-1} \cdot c$;

performing, by the processing unit, a step for producing the estimate of the haemodynamic parameter on the basis of an estimate of a quantity of interest $\hat{d} = d_{l_F}$ produced with the iteration $l_F$, where $\hat{d}$ has dimensions L×1, and $l_F$ is positive and less than or equal to L;

producing, by the processing unit, the estimate of the haemodynamic parameter in a format suitable for display on a man-machine interface; and displaying, on the man-machine interface, an illustration of the estimate.

2. The method according to claim 1, further comprising:

performing, by the processing unit, the step for producing $\tilde{A}_l^{-1}$, 0<l≤L, after the step where A is broken down canonically into singular values.

3. The method according to claim 1, further comprising:

prior to each step in order to produce dl, verifying, by the processing unit, a regularisation condition, said method being interrupted with the iteration lF as soon as said condition is met, the estimate of d being $\hat{d} = d_{l_F}$.

4. The method according to claim 3, wherein the regularisation condition comprises the calculation of an oscillation index $OI_l$, said regularisation condition being met as soon as $OI_{l_F} \leq POI$, POI being a sole predetermined value.

5. A method implemented by a processing unit of a medical imaging analysis system for producing an estimate of a haemodynamic parameter in a dynamic artery/tissue/vein system, on the basis of experimental intensity signals S(t), wherein the method comprises:

obtaining a signal S(t), wherein said signal S(t) represents the evolution of a voxel of interest of a plurality of voxels over time t, wherein the plurality of voxels constitute elementary volumes of an organ;

deriving, from the signal S(t), a concentration curve c for the voxel of interest;

performing, by the processing unit, a step for breaking down a convolution matrix A canonically into singular values in the form $A = U \cdot S \cdot V^T$ where $S \equiv \mathrm{diag}(\sigma_1, \ldots, \sigma_L)$ is the diagonal matrix of positive singular values classified by increasing order, $V^T$ is the transpose of a matrix V, and $V=(v_{ij})$ and $U=(u_{ij})$ are two unitary and real square matrices of dimension L×L, L≥N, N being a defined number of samples, A and c respectively having dimensions L×L and L×1;

performing, by the processing unit, at least one iterative step in order with the iteration 0<l≤L to calculate the L components $d_l(i)$, i=1,L of the vector $d_l$ by $$d_l(i) = d_{l-1}(i) - \frac{v_{il}}{\sigma_l} \sum_{j=1}^{N} c_j \cdot u_{jl},$$

where $d_{l-1}(i)$, $i=1,L$ are the components of the vector $d_{l-1}$ obtained with the preceding iteration;

prior to each step for producing-$d_l$, performing, by the processing unit, the verification of a regularisation condition consisting of the calculation an oscillation index $OI_l$, said regularisation condition being met as soon as $OI_{l_F} \leq POI$, where POI is a sole predetermined value, said method being interrupted with the iteration $l_F$ as soon as said condition is met;

performing, by the processing unit, a step for producing the estimate of the haemodynamic parameter on the basis of an estimate of a quantity of interest $\hat{d}=d_{l_F}$ with the iteration $l_F$ being strictly positive and less than or equal to L, where $\hat{d}$ has dimensions L×1;

producing, by the processing unit, the estimate of the haemodynamic parameter in a format suitable for display on a man-machine interface; and displaying, on the man-machine interface, an illustration of the estimate.

6. The method according to claim 3, further comprising:
performing, by the processing unit, a step for producing $d_0 = 21_{/0}^{-1} \cdot c$.

7. The method according to claim 4, wherein the oscillation index is calculated such that $$OI_l \equiv \frac{1}{L} \frac{1}{\max_{i=1,L} d_l(i)} \sum_{i=3}^{L} |d_l(i) - 2d_l(i-1) + d_l(i-2)|.$$

8. The method according to claim 4, wherein the oscillation index is calculated such that $$OI_l \equiv \frac{1}{\Delta t^2 \cdot L} \frac{1}{\max_{i=1,L} d_l(i)} \sum_{i=3}^{L} |d_l(i) - 2d_l(i-1) + d_l(i-2)|$$

where $\Delta t$ is the sampling period of the signals S(t).

9. The method according to claim 1, wherein the convolution matrix A is block-circulant with dimension L×L defined by $$A = \Delta t \cdot \begin{pmatrix} C_a(t_1) & 0 & \ldots & C_a(t_N) & \ldots & C_a(t_2) \\ \vdots & C_a(t_1) & & & \ddots & \vdots \\ C_a(t_N) & & \ddots & & & C_a(t_N) \\ 0 & \ddots & & \ddots & & 0 \\ \vdots & \ddots & \ddots & & \ddots & \vdots \\ 0 & \ldots & 0 & C_a(t_N) & \ldots & C_a(t_1) \end{pmatrix},$$

being the sampling period, $C_a(t)$ being a concentration of the contrast agent.

10. A processing unit including memory means, means for communicating with the outside world and processing means, wherein:
the means for communication are capable of receiving from the outside world an experimental data item c describing a concentration curve of a contrast agent in an elementary volume—referred to as a voxel—of an organ;
the processing means are adapted in order to implement a method for producing an estimate of a haemodynamic parameter according to claim 1.

11. The processing unit according to claim 10, wherein the communication means deliver the estimate of a haemodynamic parameter in a format appropriate to a man-machine interface suitable for displaying the estimate of the haemodynamic parameter to a user.

12. A medical imaging analysis system including a processing unit according to claim 10 and a man-machine interface suitable for displaying, to a user, the haemodynamic parameter estimated by said processing unit.

13. The method of claim 1, further comprising:
obtaining, by the processing unit, a sequence of images produced by a medical imaging apparatus, wherein each image of the sequence of images comprises the plurality of voxels from which the signal S(t) is obtained.

14. The method of claim 5, further comprising:
obtaining, by the processing unit, a sequence of images produced by a medical imaging apparatus, wherein each image of the sequence of images comprises the plurality of voxels from which the signal S(t) is obtained.

\* \* \* \* \*